United States Patent [19]

Smolin et al.

[11] 4,439,535

[45] * Mar. 27, 1984

[54] ZEOLITE ADSORBENT FOR SEPARATION OF PARA-XYLENE

[75] Inventors: William Smolin, Fishkill; John H. Estes, Wappingers Falls, both of N.Y.

[73] Assignee: Texaco Inc., White Plains, N.Y.

[ * ] Notice: The portion of the term of this patent subsequent to Sep. 28, 1999 has been disclaimed.

[21] Appl. No.: 414,287

[22] Filed: Sep. 3, 1982

[51] Int. Cl.$^3$ ............................................. B01J 29/06
[52] U.S. Cl. .................................................... 502/62
[58] Field of Search .......................... 252/430, 455 Z; 585/828

[56] References Cited

U.S. PATENT DOCUMENTS

| | | | |
|---|---|---|---|
| 4,306,962 | 12/1981 | Estes | 252/455 Z |
| 4,351,981 | 9/1982 | Smolin | 585/828 |
| 4,368,347 | 1/1983 | Carra et al. | 585/828 |

*Primary Examiner*—Carl F. Dees
*Attorney, Agent, or Firm*—Robert A. Kulason; Robert Knox, Jr.; Carl G. Seutter

[57] ABSTRACT

Para-xylene may be recovered as raffinate by contacting a C-8 aromatic hydrocarbon mixture, in the presence of toluene desorbent, with a synthetic crystalline sodium aluminosilicate zeolite HP, containing pyridine in amount of at least about 3.3 wt. % of said zeolite, having a lattice constant of 25.02–25.10Å.

4 Claims, 1 Drawing Figure

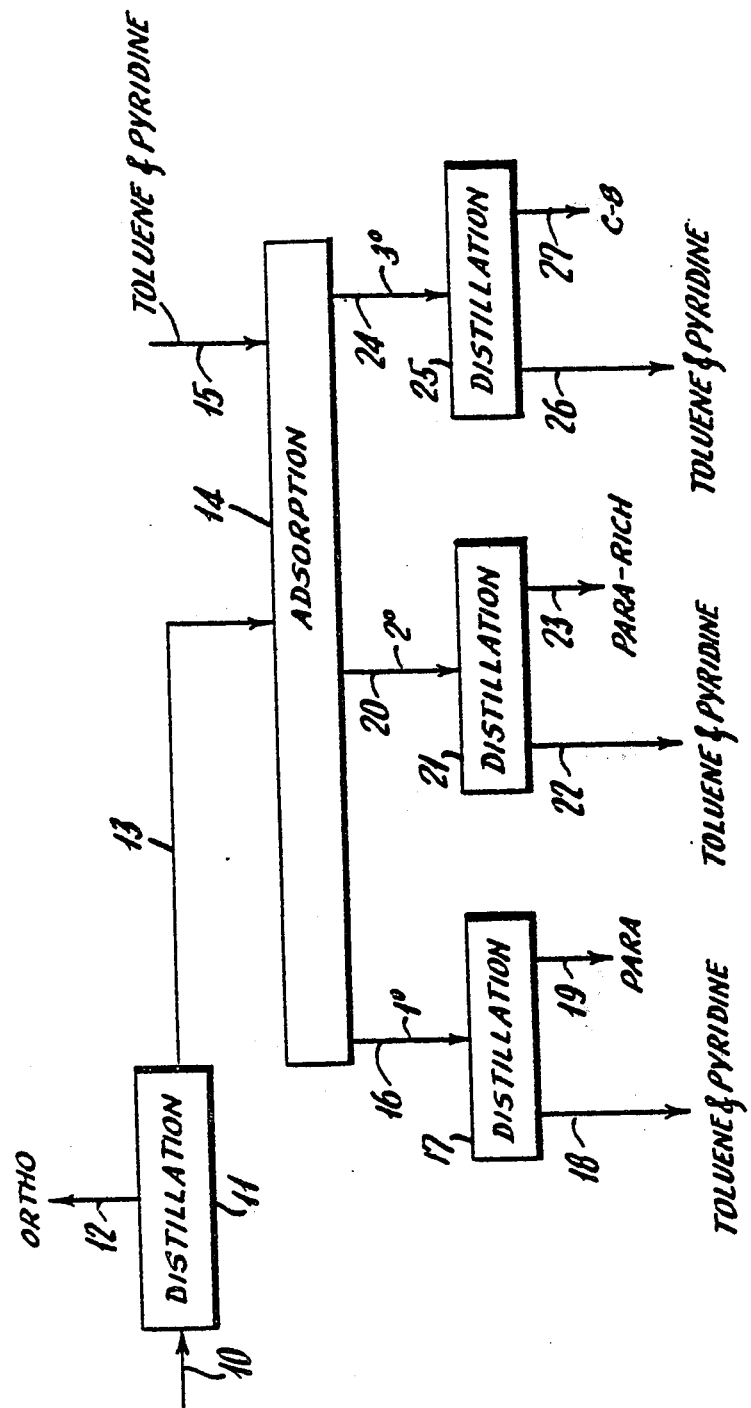

ZEOLITE ADSORBENT FOR SEPARATION OF PARA-XYLENE

FIELD OF THE INVENTION

This invention relates to solid-bed adsorptive separation. More particularly, it relates to the separation of p-xylene from C-8 aromatic hydrocarbon streams as a least strongly adsorbed, or front end raffinate product.

DESCRIPTION OF THE PRIOR ART

Solid bed adsorption techniques have been used to separate individual hydrocarbon isomers from charge hydrocarbon streams typified by C-8 aromatic streams containing ethylbenzene and xylene isomers.

Separation of para-xylene from other charge streams has been described in U.S. patents including:

| | | |
|---|---|---|
| 3,558,730 | 3,761,533 | 3,960,774 |
| 3,558,732 | 3,795,711 | 3,997,620 |
| 3,626,020 | 3,855,333 | 4,029,717 |
| 3,663,638 | 3,878,127 | 4,031,155 |
| 3,686,342-3 | 3,878,129 | 4,051,192 |
| 3,696,107 | 3,894,109 | 4,069,172 |
| 3,734,974 | 3,943,183-4 | 4,313,015 |

In these illustrative patents, particular zeolites may be used to selectively adsorb para-xylene from feed mixtures which contain several C-8 aromatic isomers; and in these patents the p-xylene is selectively adsorbed and is ultimately recovered as a tail-end or extract product while the remaining xylenes and ethylbenzene are recovered as front-end or raffinate components.

In other patents, typified by U.S. Pat. No. 3,997,619, there are disclosed processes for recovering ethylbenzene wherein this component is relatively unadsorbed and is thus recovered as high purity front-end product, the xylene isomers being recovered as tail-end products—this being effected by use of an adsorbent which is "all xylene" selective.

It is an object of this invention to provide a process for separating p-xylene as front-end or raffinate product from a C-8 charge stream. Other objects will be apparent to those skilled in the art.

STATEMENT OF THE INVENTION

In accordance with certain of its aspects, this invention is directed to a process for separating para-xylene from a feed mixture containing C-8 aromatic hydrocarbons including para-xylene which comprises contacting said feed mixture with, as an adsorbent, a sodium aluminosilicate zeolite HP containing a pyridine in at least about 3.3 wt.% of said zeolite, having a lattice constant of 25.02–25.10 Å and a ratio of silicon atoms to aluminum atoms in the unit cell below 1.0, thereby selectively adsorbing substantially all of said C-8 aromatic hydrocarbons to the substantial exclusion of para-xylene; and recovering said para-xylene as a raffinate stream.

DESCRIPTION OF THE INVENTION

The charge mixtures which may be treated by the process of this invention include mixtures containing C-8 aromatic hydrocarbons including para-xylene. These mixtures, which contain substantial quantities of ethylbenzene and the xylene isomers, generally are produced by reforming and isomerization processes which are well known to the refining and petrochemical arts. In reforming processes, a naphtha feed may be contacted with a platinum-halogen-containing catalyst at severities selected to produce an effluent containing C-8 aromatic isomers. Generally the reformate is then fractionated to concentrate the C-8 aromatic isomers in a C-8 fraction. The C-8 aromatic isomers may then be further concentrated by solvent extraction processes. Xylene isomerization processes isomerize at isomerization conditions a xylene mixture which is deficient in one or more isomers to give an effluent containing approximately equilibrium quantities of the C-8 aromatic isomers. The equilibrium composition of the xylene isomers and ethylbenzene at various temperatures are shown in the Table below.

TABLE

| EQUILIBRIUM C-8 AROMATIC COMPOSITIONS* | | | |
|---|---|---|---|
| Temperature °F. | 620 | 800 | 980 |
| | Mole percent of isomers | | |
| Ethylbenzene | 6 | 8 | 11 |
| Para-xylene | 22 | 22 | 21 |
| Meta-xylene | 50 | 48 | 45 |
| Ortho-xylene | 22 | 28 | 23 |

(*based on API sources)

Feed streams may contain ethylbenzene and any of the xylene isomers in addition to para-xylene. Extracted C-8 reformate fractions and isomerates from xylene isomerization processes containing all of the xylene isomers can be charged as feed streams. Feed streams include effluent streams from processes which have removed varying amounts of one or more xylene isomers or ethylbenzene. As an example, at least a portion of the ortho-xylene may have been previously removed by fractionation from a feed mixture containing the xylene isomers. Ortho-xylene has a boiling point of about 6° F. higher than that of the nearest other C-8 aromatic (meta-xylene) and hence can be removed as a bottoms product from ortho-xylene fractionator towers. The concentration of ortho-xylene in the effluent from this fractionation process which can be used as a feed stream may be less than the concentrations of either para-xylene or meta-xylene.

Ethylbenzene, which has a lower boiling point than any of the xylene isomers, may also be separated by distillation, preferably after removal of at least a portion of the ortho-xylene. The concentration of ethylbenzene in the effluent from this fractionation process which can be used as a feed stream may be less than the concentrations of either para-xylene or meta-xylene. Removal of ethylbenzene and/or ortho-xylene from C-8 aromatic mixtures may be effected by distillation.

C-8 aromatic components, other than those desired as product, should be present in the feedstock at as low a concentration level as possible. Thus for para-xylene production, the content of meta-xylene, ortho-xylene, and ethylbenzene should be as low as possible. For production of both para-xylene and meta-xylene, it is desirable to maintain the content of ortho-xylene and ethylbenzene as low as possible. In practice, only ortho-xylene and ethylbenzene can be removed by distillation, so a charge stock containing a concentrate of meta-xylene and para-xylene would be typically available for production of either para-xylene or para-xylene and meta-xylene. It is to be noted that separation of ethylbenzene by distillation is expensive; and accordingly economic considerations may dictate that the feedstock would have been treated in a manner to principally reduce the content of ortho-xylene.

In accordance with practice of the process of this invention, the feed mixture containing C-8 aromatic hydrocarbon including para-xylene may be contacted with, as an adsorbent, a sodium zeolite HP containing a pyridine, thereby selectively adsorbing substantially all of said C-8 aromatic hydrocarbon to the substantial exclusion of para-xylene.

The synthetic crystalline sodium aluminosilicate zeolite HP adsorbents which may be employed in practice of the process of this invention may include those which are made at high pressures at moderate temperatures and which are particularly characterized by a lattice constant of 25.02–25.10 Å and by a ratio of silicon atoms to aluminum atoms of below 1.0. Typical of the sodium HP zeolites may be those prepared as disclosed in U.S. Pat. No. 4,289,740 which issued Sept. 15, 1981 to Texaco Inc. as assignee of John H. Estes, or U.S. Pat. No. 4,306,962 which issued Dec. 22, 1981 to Texaco Inc. as assignee of John H. Estes.

The synthetic crystalline sodium aluminosilicate zeolite HP (NaHP zeolite) may be prepared by forming an aqueous solution containing sodium aluminosilicate ($Na_2O$—$SiO_2$—$Al_2O_3$) in amounts and ratio sufficient to yield a product zeolite having a ratio of silicon atoms to aluminum atoms of below 1.0, typically 0.8–1.0.

The mixture may preferably be aged at pressure above 20,000 psig. More preferably aging is carried out at pressure above 40,000 psig. Although aging may be carried out at 20,000–80,000 psig, it is preferably effected at 20,000–60,000 psig, say 40,000–50,000 psig, commonly about 50,000 psig. Aging may be carried out at room temperature up to 100° F., preferably 70° F. for 8–24 hours, preferably 16 hours.

The mixture, preferably after aging, is subjected to HP zeolite-forming pressure of 20,000–80,000 psig, preferably 20,000–60,000 psig, say 40,000–50,000 psig, commonly about 50,000 psig. Temperature of operation may be 150° F.–350° F., preferably 150° F.–250° F., say 200° F. over 8–16 hours, say 8 hours. In the preferred embodiment, the pressure will be the same in the aging step (if and when employed) as it is in the subsequent reaction step.

The typical NaHP zeolites obtained by recovery of the product from the reaction may have the following formula:

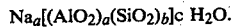

$Na_a[(AlO_2)_a(SiO_2)_b]c\ H_2O$.

In this formula a plus b is 192. a is greater than 96 and preferably 97–108. In the formula, c is commonly 264.

A typical NaHP zeolite may have the formula:

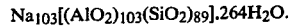

$Na_{103}[(AlO_2)_{103}(SiO_2)_{89}].264H_2O$.

The NaHP zeolite so-prepared is commonly typified by a ratio of silicon atoms to aluminum atoms of below 1.0, preferably 0.8–1, say 0.98 and by a lattice constant of preferably 25.02–25.10 Å, say 25.08 Å.

In practice of the process of this invention according to certain of its aspects, adsorption is effected with a sodium high pressure zeolite containing pyridine se or a substituted pyridine selected from the group consisting of 1-picoline, 3-picoline, 4-picoline, 2,4-lutidine, 2,6-lutidine, and 3,4-lutidine. Although it may be possible to obtain separation of para-xylene by the use of other pyridines, such as the picolines (including 2-picoline or 3-picoline, or 4-picoline), or the lutidines (including 2, 4-lutidine or 2,6-lutidine, or 3,4-lutidine), it is found that most effective operation may be achieved by the use of pyridine se.

The organic selectivity modifier (preferably pyridine) may be contained in the zeolite in amount of about 10%–60% of the total adsorptive capacity (C-8 aromatic plus modifier) of the zeolite. The capacity of NaHP-type zeolite, expressed as weight % of adsorbed component(s) relative to weight of dry adsorbent, may typically be 10–25 with many falling in the 13–23 range. Total capacity may be essentially equivalent for C-8 aromatics, pyridine, and their mixtures. The pyridine loading is typically in the range of 3.3–20 wt. %, preferably 3.3–8 wt. %, say about 5 wt. % of the amount of zeolite adsorbent.

Thus, the weight ratio of pyridine to total capacity of the zeolite may be of the order of 0.1–0.6 or more, say 0.2–0.5.

A typical instance may utilize a pyridine loading of 5.0% (of the adsorbent) where the adsorbent may have a total capacity of 16.5% corresponding to a ratio of 0.30.

In one embodiment, the pyridine is loaded onto the zeolite adsorbent prior to initiation of operation; and this may commonly be effected by contacting the pyridine modifier with the adsorbent before the latter is admitted to the reaction vessel. Preferably, the modifier is mixed with, or dissolved in, the desorbent to be used in the process as hereinafter described and the adsorbent is submerged in the mixture. At room temperature, pyridine is substantially completely removed from solution by the zeolite.

The adsorbent can be contained in one or more chambers where through programmed flow into and out of the chamber separation of the isomers is effected. Preferably in operation, fixed quantities of a charge stream and of a desorbent stream (both preferably anhydrous) are admitted alternately to one end of a bed or column of zeolite; and effluent from the other end of the column is segregated into cuts. The bed may be operated in either up-flow or down-flow mode. Concentrations of individual charge components and of desorbent in effluent from the columns resulting from this operation vary with time (or quantity of total effluent). The resolution of components taking place in the column is characterized as a cyclic, chromatographic, adsorptive separation where the cycle time is the interval between the start of introduction of corresponding successive portions of charge (or of desorbent) to the column, or their appearance in the effluent. Effluent from the column during each cycle is segregated into fractions, or cuts, which may include (1) a front end or raffinate cut or product cut taken at the beginning of the cycle in which the least strongly adsorbed charge component (para-xylene) is concentrated to high purity relative to other charge components; (2) one or more intermediate cuts in which the front end product component is concentrated relative to other charge components, but at a lower purity level than in the front end cut (such cuts may be recycled to the charge preparation operation to permit substantially complete recovery of product component(s) in high purity); and (3) one or more cuts in which only small amounts of product component(s) are present. If desired, cut(s) (2) may be combined with cut(s) (3).

The cyclic process may be carried out either in the liquid phase or in the vapor phase. Liquid phase operation may be carried out at lower temperatures and may permit easier control of charge and cut points, but vapor phase operation is preferred because of the much greater separation efficiency afforded by this mode. Preferred conditions for the process of this invention in liquid phase operation will include temperatures within the range from about 100° to about 450° F. at pressures sufficient to maintain a liquid phase and to provide a driving force for moving fluid through the adsorbent bed, generally in the range from about atmospheric to about 500 psig. Preferred conditions for the process of this invention in vapor phase operation will include temperatures from about 290° F. to about 450° F. sufficient to maintain components in the vapor phase at pressures from about atmospheric to about 80 psig, the pressure preferably being the minimum required to drive fluid through the system.

In both liquid and vapor phase modes, operation is substantially isothermal; and pressure drop across the system is substantially constant, although some variation may occur during the course of a cycle. The quantity of desorbent introduced for a given quantity of charge is sufficient to displace all charge components to an extent that the residual total charge component concentration in the effluent for a given cycle is very low, preferably below about 0.1%, before charge components from the following cycle start to appear. This determines the minimum preferred desorbent: charge ratio; if less desorbent is used, product purity in subsequent cycles is reduced. If more desorbent is used, separation is still achieved, but the cycle time and amount of desorbent to be removed from product fractions are unnecessarily increased. The quantity of charge introduced per cycle and the minimum desorbent: charge ratio for this quantity of charge are related to a number of factors including adsorbent capacity, selectivity, and particle size, fluid flow rate, and particularly to charge composition and to column length. Preferred process design specifications are largely related to the cost of the absorbent bed per unit of pure product production rate and to the cost of separating desorbent from effluent fractions; both costs must be considered together.

The process of this invention may also be effected in a simulated moving bed countercurrent system. The operating principles and sequence of such a flow system are described In U.S. Pat. No. 2,985,589 issued to D. B. Broughton which patent is incorporated herein by specific reference thereto. This system may be operated in the liquid phase mode with the same zeolite HP adsorbents and in the same temperature and pressure ranges as those previously described for cyclic operation in the liquid phase mode. Para-xylene is recovered as a least strongly adsorbed, or raffinate product. Operation of a simulated moving bed countercurrent system in the vapor phase mode, while possible in principle, would be difficult to achieve in practice; so if the advantageous separation efficiency of the vapor phase mode is to be obtained, the cyclic operating procedure is preferred.

The desorbent materials which are used in the preferred processing schemes employed may vary depending on the type of operation employed. The term "desorbent material" as used herein means any fluid substance capable of removing a selectively adsorbed feed component from the adsorbent. In the swing-bed system, in which the selectively adsorbed feed component is removed from the adsorbent by a purge stream, desorbent materials comprising gaseous hydrocarbons such as methane, ethane, etc., or other types of gases such as nitrogen or hydrogen may be used at elevated temperatures or reduced pressures or both to effectively purge the adsorbed feed component from the adsorbent.

However, in adsorptive separation processes which employ zeolite adsorbents and which are generally operated at substantially constant pressures and temperatures, the desorbent material relied upon must be judiciously selected to satisfy several criteria. First, the desorbent material must displace the adsorbed feed component from the adsorbent with reasonable mass flow rates without itself being so strongly adsorbed as to unduly prevent charge components from displacing the desorbent material in a following adsorption cycle. Secondly, desorbent materials must be compatible with the particular adsorbent and the particular feed mixture. More specifically, they must not reduce or destroy the critical selectivity of the adsorbent for the components of the charge.

Desorbent materials to be used in the process of this invention should additionally be substances which are easily separable from the feed mixture that is passed into the process. Each of the effluent cuts in cyclic processes, and both raffinate and extract streams in simulated moving bed countercurrent processes, contain desorbent in admixture with charge components. Without a method such as distillation, for separating desorbent material the product purity would be low; and consumption of desorbent in the process would be excessive. Any desorbent material used in this process will have a substantially different average boiling point from that of the feed mixture. The use of desorbent material having a substantially different average boiling point than that of the feed allows separation of desorbent material from feed components in the various effluent cuts or the extract and raffinate streams by fractionation thereby permitting reuse of desorbent material in the process. The term "substantially different" as used herein means that the difference between the average boiling points between the desorbent material and the feed mixture shall be at least 15° F. The boiling range of the desorbent material may be higher or lower than that of the feed mixture.

Among the desirable characteristics of an adsorbent are: adsorptive capacity for some quantity of an extract component per unit quantity of adsorbent; the selective adsorption of feed components with respect to one another such that a desired pure product component is adsorbed more strongly or less strongly than the other components; and sufficiently fast rates of adsorption and desorption of the extract components to and from the adsorbent.

Capacity of the adsorbent for adsorbing components of the separation system, including desorbent, is, of course, a necessity; without such capacity the adsorbent is useless for adsorptive separation. Increased capacity of a particular adsorbent makes it possible to increase the separation efficiency and thereby reduce the amount of adsorbent needed to effect separation of a particular feed mixture at a given product purity and yield. (Yield is defined as the fraction of a feed component recovered as pure product.) A reduction in the amount of adsorbent required for a specific adsorptive separation reduces the cost of the separation process. It is important that the good initial capacity of the adsorbent be maintained during actual use in the separation process over some economically desirable life.

The second necessary adsorbent characteristic is the ability of the adsorbent to separate components of the feed; or, in other words, that the adsorbent possess adsorptive selectivity for one component as compared to another component. Relative selectivity can be expressed not only for one feed component as compared to another but can also be expressed between any feed mixture component and the desorbent material. The selectivity as used throughout this specification is defined as the ratio of concentrations of the two components in the adsorbed phase divided by the ratio of concentrations of the same two components in the unadsorbed phase at equilibrium conditions.

Determining these adsorbent characteristics, particularly capacity and selectivities for charge and desorbent components, is essential for developing an adsorptive separation system for recovering specific pure components from mixtures with difficulty separable substances, such as isomers of the desired products. Further, once such a system is established, a convenient test method is required for determining that subsequent batches of adsorbent are equivalent to the original adsorbent or fall within a satisfactory range. I have found a convenient and effective procedure for accomplishing these objectives which comprises the steps of:

(1) Combining a suitably prepared (i.e. dried to a specific moisture level) adsorbent sample with a test mixture of test components, which may include components of a mixture to be separated, desorbent materials, and adsorbent modifiers, in the presence of a reference component which is essentially unadsorbed and essentially inert, in the presence of strongly adsorbed test components. For determining adsorption equilibria for mixtures of aromatic hydrocarbons, paraffinic or cycloparaffinic hydrocarbons are suitable reference components. A particularly suitable reference component is cyclohexane.

(2) Equilibrating the solid-liquid mixture with suitable agitation in a sealed vessel at a convenient temperature, which may be room temperature.

(3) Separating equilibrated liquid from solid adsorbent (eg by centrifuging), sampling the liquid, and analyzing the liquid by a suitable procedure (eg gas chromatography) for determining the concentration of each of the components present.

(4) From the known weight and composition of the test component-reference component test mixture charged, and composition of equilibrium liquid, calculating the quantity of each test component in the equilibrium liquid using as a basis for such calculation the originally charged weight of inert (non-adsorbed) reference component in both the test liquid and equilibrium liquid.

(5) By difference, from the calculated weight of each component in the equilibrium liquid and the known amount of each component in the charge, calculating the weight of each test component adsorbed.

(6) From the weight of adsorbent charged and the weights of test components adsorbed, calculating the capacity of the adsorbent for the test components and the composition of the adsorbed phase.

(7) From the calculated composition of the adsorbed phase and the composition of the equilibrium liquid phase obtained by analysis, determining selectivity of the adsorbent for any pair of test components.

The method may be used to screen separation systems prior to column operation; separations obtained from column operation at elevated temperatures are found to correspond to those expected from the adsorbent characteristics determined by the test method. It may be used to determine variation of selectivity with fluid phase composition, a relationship not readily obtainable from other methods for estimating adsorbent selectivities. It may be used to determine the effects of components added to modify the selectivity characteristics of original adsorbents or to determine the effects of impurities (such as water) which may be present in charge or desorbent streams, particularly in commercial operation. It may be used to determine variations of adsorbent capacity, which may be due to occluded solid material in the pores or to variations in the quantity of binder used, which do not appreciably affect adsorbent selectivity. It may be used as an adsorbent specification test where specific values or ranges of capacity and selectivity for specific test components at particular concentration levels are specified. It may be used to select suitable desorbent materials. It may also be used as a control test during manufacture of zeolites.

The preferred desorbent may be toluene. Benzene may be employed as desorbent.

In isothermal, isobaric, operation of the process of my invention, I have found that desorbent materials comprising mono-cyclic-aromatic hydrocarbons are particularly effective. Specifically, desorbent materials comprising toluene are preferred for this type of operation.

In operation of the process of this invention in the preferred cyclic, liquid phase mode, the NaHP zeolite (pyridine-loaded) packed in the adsorption column, is flooded with desorbent e.g. toluene which is passed downwardly through the adsorbent bed at a flow rate of 0.1–6, say about 2 gallons per minute per square foot of column cross section. Periodically the flow of toluene is interrupted and a portion of charge is introduced at about the same flow rate. Pyridine, is preferably added with the desorbent toluene to balance pyridine removed from the adsorbent bed in the column effluent; the amount added depends on the pyridine loading of the adsorbent and the temperature of the adsorption column—typically it may be 0.01%–1.0%, say 0.2% of the desorbent toluene. As the effluent is monitored (by gas chromatography, for example), toluene desorbent is first observed. When the first C-8 component shows, which in this process is para-xylene, the cycle is considered started. Operation is carried out so that the NaHP zeolite contains at least about 3.3 wt.% of the pyridine.

It is possible to collect incremental portions of product (over equal time increments), but preferred operation is carried out by collecting the entire yield of high purity (i.e. 99+% purity) para-xylene in one aliquot. Depending on the details of the downstream processing facility, there may be recovered a second product stream which is rich in para-xylene although it is of a purity less than that of the first product stream. A third stream may be recovered which contains a mix of C-8 components.

Each of these product streams may be separated, as by distillation, from the toluene and pyridine. Pyridine and toluene are recovered together and may be recycled.

Operation in the vapor phase is comparable. The absorbent may be loaded with pyridine and toluene in liquid phase ab initio. The system is then heated to e.g. 340° F. and liquid displaced from the column by passing vapor phase toluene desorbent (containing added pyridine) downwardly through the adsorbent bed. Charge is introduced periodically in the vapor phase. The effluent is condensed and collected in desired increments followed by recovery of the desired high purity para-xylene from toluene and pyridine in the front end product.

ADVANTAGES OF THE INVENTION

It is a feature of the process of this invention that it is characterized by many advantages including the following:

(i) it permits attainment of p-xylene as a front-end product which is typically more easily purified than is the tail-end product, and which may be recovered as product having a very low level of C-8 impurities;

(ii) it permits operation under conditions of high selectivity;

(iii) selectivity increases as the concentration of less strongly adsorbed component increases, and thus operation at the front-end of the adsorption cycle permits higher selectivity to be realized as the proportion of p-xylene in C-8 aromatics increases in this portion of the cycle; and (iv) the content of impurities, originating from the tail of a preceding cycle, is measured against a high front-end product peak and, even under the least favorable conditions of operation, causes a smaller loss of product purity than would the internal front end components tailing into a back end product.

DESCRIPTION OF THE DRAWINGS

The drawing shows a schematic process flow sheet by means of which a C-8 hydrocarbon may be treated according to a preferred embodiment of this invention.

DESCRIPTION OF PREFERRED EMBODIMENTS

Practice of the novel process of this invention may be apparent to those skilled in the art from the following description of various embodiments wherein as elsewhere in the description, all parts are parts by weight unless otherwise specified.

EXAMPLES I-1 TO I-14

In these examples, equilibrium data were obtained for adsorption of C-8 aromatic isomers on various HP zeolite samples both in their original form and containing pyridine.

Adsorbents used were dried in a tube furnace under a flow of dry nitrogen, and then were loaded into previously weighed glass ampoules in a nitrogen-flushed dry box. The weight of adsorbent was determined, and then a quantity of previously prepared charge mixture was introduced, the ampoule was chilled in liquid nitrogen, evacuated, sealed, and weighed to determine the weight of charge mixture. Charge mixtures were made up with known amounts of C-8 aromatics, inert reference component (cyclohexane), and in designated instances, pyridine. The ratio of reference component to total C-8 aromatics (and desorbent, if present) was generally 1.0–1.5:1. Pyridine (when present) was present in an amount sufficient to give a desired ratio of pyridine/dry adsorbent. The weight ratio of liquid charge to adsorbent was normally about 2 and the quantity of adsorbent used was generally about 1 gram.

Loaded ampoules were agitated on a shaker table at a temperature of about 75° F. for an equilibration period. Typically the equilibration period was about one week up to several months, but equilibration was probably substantially complete after one to two days. After equilibration, ampoules were usually centrifuged to facilitate separation of liquid from adsorbent, then the liquid was sampled and analyzed by gas chromatography. Replicate analyses were usually obtained and analyses of samples of charge liquid (retained in sealed ampoules) were usually carried out at the same time.

The quantity of each C-8 aromatic (and desorbent, if present) in the equilibrium liquid was calculated from the GC analysis and known weight of reference component in the charge as $$\text{Wt. Component (Equil.)} = \frac{\text{\% Component (Equil.)}}{\text{\% Reference (Equil.)}} \times \text{Wt. Reference (Charge)}$$

The corresponding quantity of component adsorbed per unit weight of adsorbent charged was calculated as:

$$\frac{\text{Wt. Component Adsorbed}}{\text{Wt. Adsorbent}} = \frac{\text{Wt. Component (Equil.)} - \text{Wt. Component (Charge)}}{\text{Wt. Adsorbent}}$$

Pyridine loading of the adsorbent (per unit weight of adsorbent) was calculated on the basis of complete pyridine adsorption as:

$$\text{Pyridine Loading} = \frac{\text{Wt. Pyridine (Charge)}}{\text{Wt. Adsorbent}}$$

The gas chromatographic procedure used for sample analysis was not suitable for pyridine analysis, but measured nitrogen concentrations indicate that the amount of pyridine in the equilibrium liquid is negligible.

Total capacity of the adsorbent is the sum of individual component adsorption values plus the pyridine loading. Composition of the C-8 aromatics (and desorbent, if present) in the adsorbed phase is calculated from the individual component adsorption values.

The selectivity with which an adsorbent adsorbs one component relative to another is a measure of its separation capability. Selectivity factors alpha ($\alpha$) are commonly used as measures of adsorbent selectivity between components of a mixture. Selectivity between any two components is defined as:

$$\alpha = \frac{\left(\frac{\text{Conc. Component 1}}{\text{Conc. Component 2}}\right)_{\text{Adsorbed Phase}}}{\left(\frac{\text{Conc. Component 1}}{\text{Conc. Component 2}}\right)_{\text{Fluid Phase}}}$$

Thus $\alpha$ will be greater than 1.0 if component 1 is more strongly adsorbed than component 2. With a multi-component mixture it is convenient to express selectivities of the components relative to a particular component of the mixture.

Selectivity factors in the present examples are calculated from the composition of the adsorbed phase, determined as described above, and the composition of the equilibrium liquid determined by gas chromatography.

In each of Examples I-1 to I-14, a charge liquid containing equal portions by weight of ethylbenzene, p-xylene, m-xylene, and o-xylene (plus cyclohexane reference component) was equilibrated against a designated HP zeolite. When pyridine was present, it is reported as weight percent of adsorbent.

The following table sets forth equilibrium data at 75° F. on various HP zeolites—both with and without pyridine modifier. The Pyridine Loading is expressed as weight percent of the dry adsorbent, as charged. Capacity of the zeolite (total and C-8) is expressed as weight % adsorbed component(s) based on the weight of adsorbent.

There are tabulated the selectivity (alpha) of (i) EB (ethylbenzene) with respect to p-xylene; (ii) P-X (para-xylene) with respect to p-xylene, which is of course 1.00, included for reference; (iii) M-X (meta-xylene) with respect to p-xylene; and (iv) O-X (ortho-xylene) with respect to p-xylene.

TABLE

EQUILIBRIUM DATA - HP ZEOLITES
WITH AND WITHOUT PYRIDINE MODIFIER (75° F.)

| Example | Pyridine Loading | HP Zeolite | Capacity Total | C-8 | Selectivity EB | P | M | O |
|---|---|---|---|---|---|---|---|---|
| I-1* | 0 | Na | 10.4 |  | 1.27 | 1.00 | 1.00 | 1.00 |
| 2* | 0 | Na | 16.4 |  | 1.13 | 1.00 | 0.93 | 1.05 |
| 3* | 0 | Na | 16.5 |  | 1.13 | 1.00 | 0.97 | 0.95 |
| 4* | 0 | Na | 13.5 |  | 1.28 | 1.00 | 1.01 | 1.08 |
| 5* | 0 | Na | 17.1 |  | 1.15 | 1.00 | 0.99 | 0.98 |
| 6* | 0 | K | 15.4 |  | 1.46 | 1.00 | 0.49 | 0.74 |
| 7* | 2.9 | Na | 9.7 | 6.8 | 2.06 | 1.00 | 1.80 | 0.97 |
| 8* | 2.9 | Na | 7.8 | 4.9 | 3.02 | 1.00 | 2.50 | 0.96 |
| 9 | 5.9 | Na | 16.2 | 10.3 | 2.03 | 1.00 | 2.56 | 1.35 |
| 10 | 5.8 | Na | 16.5 | 10.7 | 1.86 | 1.00 | 2.22 | 1.32 |
| 11 | 5.9 | Na | 13.9 | 8.0 | 2.32 | 1.00 | 2.72 | 1.23 |
| 12 | 5.7 | Na | 14.3 | 8.6 | 2.01 | 1.00 | 2.55 | 1.30 |
| 13 | 8.5 | Na | 14.3 | 5.8 | 1.70 | 1.00 | 2.77 | 1.26 |
| 14 | 5.5 | Na | 16.5 | 11.0 | 2.39 | 1.00 | 2.53 | 1.29 |

From the above table, it will be apparent to those skilled in the art that the novel technique of this invention permits attainment of raffinate containing substantially pure para-xylene. For example, runs I-1* to 6* using pyridine-free NaHP and KHP zeolites demonstrate that it is not possible to attain para-xylene as raffinate. In Run I-1* there is obtained no measurable separation between ortho-, meta-, and para-. In control runs I-7* and I-8*, wherein the pyridine content is below the preferred minimum of about 3.3 wt.%, there is substantially no separation between the ortho- and the para-.

Results comparable to Examples I-9 through I-14 may be attained in practice if the desorbent is:

TABLE

| Example | Desorbent |
|---|---|
| II-1 | benzene |
| -2 | toluene |
| -3 | p-diethylbenzene |

Results comparable to Examples I-9 through I-14 may be attained if the substituted pyridine is:

TABLE

| Example | Pyridine Modifier |
|---|---|
| III-1 | 2-picoline |
| -2 | 3-picoline |
| -3 | 4-picoline |
| -4 | 2,4-lutidine |

EXAMPLE IV

In this Example there is set forth the best mode known to me at this time for practicing the process of this invention. The drawing shows a schematic process flow sheet of this embodiment of the process.

In this embodiment, the charge C-8 stream from which it is desired to recover para-xylene contains

| ethylbenzene | 20.0 w % |
|---|---|
| para-xylene | 20.3 w % |
| meta-xylene | 39.7 w % |
| ortho-xylene | 20.0 w % |

This stream is admitted through line 10 to disillation operation 11 wherein there is separated pure ortho-xylene, recovered through line 12.

The composition in line 13 (1000 parts) typically may contain

| ethylbenzene | 24.7 w % |
|---|---|
| para-xylene | 25.0 w % |
| meta-xylene | 49.0 w % |
| ortho-xylene | 1.3 w % |

Adsorption operation 14 utilizes NaHP zeolite which has been loaded with 5 w% of pyridine. The outlet of the column is at atmospheric pressure. Toluene desorbent containing pyridine (in amount sufficient to prevent a net loss of pyridine during the course of the cyclic operation), is admitted in the vapor phase at 340° F. through line 15 to the top of the column and passed through the adsorption bed at a flow rate such that the quantity of toluene introduced per unit time per unit cross section of adsorbent column is equivalent to 0.5 gallons of liquid toluene (measured at room temperature) per minute per square foot of column cross section.

Periodically, the flow of toluene vapor (in this example, all references to toluene from line 15 refer to toluene containing pyridine) to the column from line 15 is interrupted and charge, in the vapor phase at 340° F., is admitted through line 13 to the top of the column and is passed through the adsorption bed at a flow rate such that the quantity of charge introduced per unit time per unit cross section of adsorbent column is equivalent to 0.5 gallons of liquid charge (measured at room temperature) per minute per square foot of column cross section. The flow of charge C-8 hydrocarbon alternates with the flow of toluene from line 15.

Alternate introduction of charge and toluene desorbent is continued, the interval between sequential introductions of charge (or of toluene) comprising a single cycle. Toluene is introduced during each cycle. A larger quantity of toluene per cycle may be used without affecting product quality, but at the expense of greater cycle time and greater cost for separating desorbent from C-8 aromatic components. Use of a smaller quantity of toluene per cycle reduces the yield of pure product.

A single complete cycle is considered here to comprise the effluent from the point where total C-8 aromatic content rises above 0.1 wt. % to the point where it falls below 0.1 wt. %. In each cycle, in which 1000 parts of charge are introduced through line 13 a first cut is taken through line 16 starting at the point where C-8 aromatic concentration reaches 0.1%. This first cut contains 145.4 parts of para-xylene to the exclusion (about 0.45 w% of the para-xylene) of other C-8 isomers, plus toluene containing pyridine. This mixture is separated by distillation in distillation operation 17 to permit recovery in line 18 of toluene and pyridine which may be recycled to line 15 with or without intermediate separation or purification. There is recovered in line 19, 146.1 parts of 99+ wt. % para-xylene.

The second cut, recovered in line 20, contains C-8 isomers of which about 51 w % is para-xylene, together with toluene and pyridine. This mixture is separated in distillation operation 21 to permit recovery in line 22 of toluene and pyridine which may be handled in manner similar to that for the comparable stream in line 18. The stream in line 23 is a para-xylene stream containing 51 w% para-xylene together with other C-8 isomers. This latter cut may be recycled, as to line 10. In the simplest mode of operation, it may be desirable to not separately recover this second cut, but to combine it with the third cut infra.

The third cut recovered in line 24 contains little of no para-xylene in this embodiment. Typically it contains C-8 components of which less than 5% is para-xylene, and toluene containing pyridine. This mixture is separated by distillation in distillation operation 25 to yield in line 26, toluene containing pyridine, this stream being handled in manner similar to streams 18 and 22, either separately or in combination therewith. There may be recovered in line 27 a C-8 stream containing in this embodiment less than 5% of para-xylene.

It will be apparent to those skilled in the art that this processing scheme may be modified depending on the concentration of the several components in the charge or upon the needs of the processor. For example, it may be desirable to recover the second and third cuts together rather than separately. The para-xylene-rich stream recovered by distillation of the second cut may be recycled to charge in line 10 or passed to a separate separation system, etc.

Although this invention has been illustrated by reference to specific embodiments, it will be apparent to those skilled in the art that various changes and modifications may be made which clearly fall within the scope of this invention.

I claim:

1. A synthetic crystalline sodium aluminosilicate zeolite HP, containing a pyridine in amount of at least about 3.3 wt.% of said zeolite having a lattice constant of 25.02–25.10 Å.

2. A synthetic crystalline sodium aluminosilicate zeolite HP, containing pyridine in amount of at least about 3.3 wt.% of said zeolite, having a lattice constant of 25.02–25.10 Å and an atomic ratio of silicon to aluminum of below 1.0.

3. A synthetic crystalline sodium aluminosilicate zeolite HP, containing a pyridine in amount of about 3.3–20 wt.% of said zeolite, having a lattice constant of 25.02–25.10 Å.

4. A synthetic crystalline sodium aluminosilicate zeolite HP, containing a pyridine in amount of at least about 3.3 wt.% of said zeolite as claimed in claim 3 wherein said pyridine is pyridine se or a substituted pyridine selected from the group consisting of 2-picoline, 3-picoline, 4-picoline, 2,4-lutidine, 2,6-lutidine, and 3,4-lutidine.

* * * * *